United States Patent [19]
Spann

[11] 3,938,205
[45] Feb. 17, 1976

[54] BODY POSITIONER

[76] Inventor: Donald C. Spann, 5 Ferncreek Court, Greenville, S.C. 29607

[22] Filed: Aug. 19, 1974

[21] Appl. No.: 498,399

[52] U.S. Cl. .................................................. 5/327 B
[51] Int. Cl.² .......................................... A47C 21/00
[58] Field of Search ........................................... 5/327

[56] References Cited
UNITED STATES PATENTS

| | | | |
|---|---|---|---|
| 1,902,361 | 3/1933 | Hamersley | 5/327 R |
| 3,333,286 | 8/1967 | Biolik | 5/327 R |
| 3,505,994 | 4/1970 | Smith | 5/327 R |
| 3,694,831 | 10/1972 | Treace | 5/327 R |
| 3,811,140 | 5/1974 | Burpo | 5/327 R |

*Primary Examiner*—Bernard A. Gelak
*Attorney, Agent, or Firm*—Bailey & Dority

[57] ABSTRACT

A body positioner and the like is formed from a block of polyurethane foam having resilient characteristics capable of deformation and of permitting the passage of air and having an unsymmetrical pentagonal cross-section and having a length substantially greater than its width so that the block may be rotated on its major surfaces to provide for a variety of adjustable continuous positioning support surfaces along a major portion of the body of a patient while lying upon an operating table or examining table.

1 Claim, 4 Drawing Figures

BODY POSITIONER

BACKGROUND OF THE INVENTION

In many instances, it is necessary to position a patient lying laterally upon an operating or examining table in an angular position relative to the table instead of a strictly supine position.

Heretofore, arrangements including a plurality of foam positioner blocks have been used as in U.S. Pat. No. 3,604,023. However, this arrangement provides only for a normal vertical side position on the table and not for rotating the patient's lateral body position to different angular positions relative to the table.

In many instances, as where the patient is under sedation, the use of a plurality of smaller spaced foam blocks would not result in stability of the patient on the table.

Foam support cushions have also been used in various shapes and sizes to support a person's body while in a strictly supine or reclined position as, for example, U.S. Pat. No. 3,333,286. These cushions differ from positioner of the present invention in that they would not present a substantial support for a patient's entire lateral body length while lying in a side-rotated position, nor would they have the adjustability afforded by positioners of the present invention for a patient while in a side-rotated position.

Accordingly, it is an important object of the present invention to provide a versatile body positioner block which has a plurality of major support surfaces to adjustably position the body of the patient while lying laterally on an operating or examining table.

Another important object of the invention is to provide a body positioner block which will create a substantial lateral support for the patient on the table to provide stability for the patient's position.

SUMMARY OF THE INVENTION

It has been found that a body positioner for a patient lying upon an operating or diagnostic examining table may be formed from a single elongated resilient, deformable polyurethane foam block of unsymmetrical pentagonal cross-section having three major surfaces and two minor surfaces to provide for adjusting and stably supporting a patient lying laterally in a variety of angular body positions relative to the table.

BRIEF DESCRIPTION OF THE DRAWING

The construction designed to carry out the invention will be hereinafter described, together with other features thereof.

The invention will be more readily understood from a reading of the following specification and by reference to the accompanying drawing forming a part thereof, wherein an example of the invention is shown and wherein.

DESCRIPTION OF A PREFERRED EMBODIMENT

Figure 1:
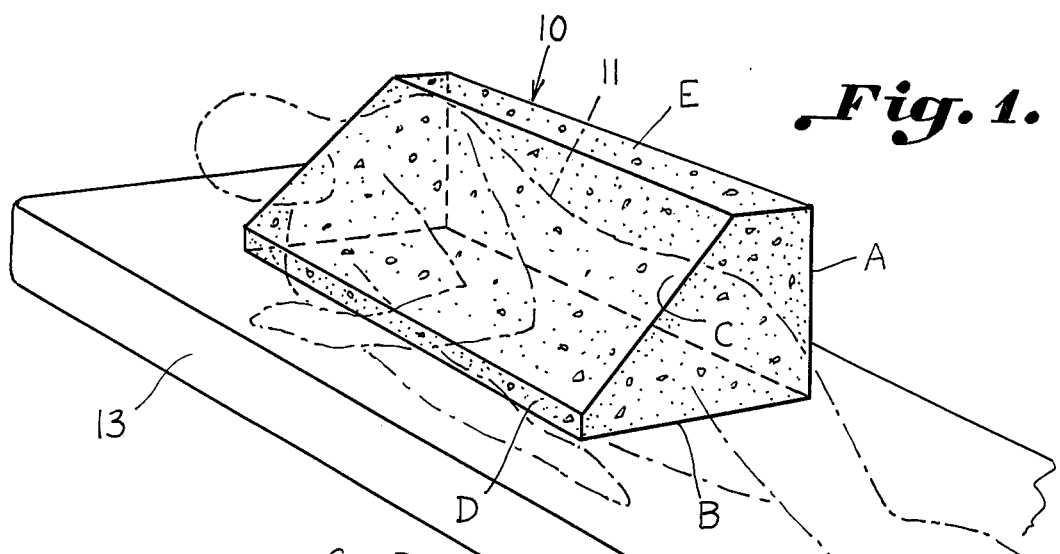
FIG. 1 is a front perspective view showing the positioning of the patient's body with a body positioner constructed in accordance with the invention in a first position.

The drawing illustrates a body positioner and the like for variably adjusting the position of and supporting a patient lying laterally upon an operating or examining table.

The body positioner of this invention includes an elongated block, broadly designated at 10, constructed of resilient deformable polyurethane foam. The foam block has the advantage of being inexpensive and suitable for one patient use.

The body positioner is formed from a solid rectangular foam block which is first cut or sawed into a triangular block having opposed 45° angles. The edges at the apex of the 45° angles become feathered as a result of inherent irregularities of the material and the sawing operation. These edges present an unsightly appearance and tend to peel away in small bits and pieces and such a block has proved to be impractical. Therefore, the triangular block is then advantageously shaped by cutting or sawing off triangular edge portions of different widths. Removing these edges by forming smooth planar minor surfaces of different widths has the advantage of giving the block a finished appearance as well as the important advantage of providing versatility to the body positioner as it is used on the operating or examining table by the nurse to provide a variety of patient body positions relative to the table.

Figure 2:
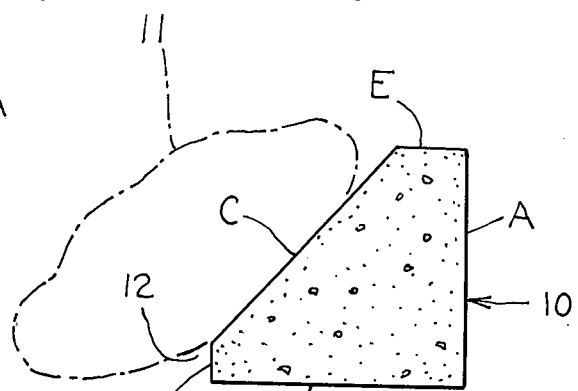
FIG. 2 is an end elevation showing the patient's body with a body positioner in a first position.

The elongated block is preferably unsymmetrical pentagonal cross-section having major planar surfaces A, B and C and minor planar surfaces D and E. The major surfaces A and B are at right angles to each other and are opposite a 45° major surface C which is joined to the major surfaces A and B by opposed minor surfaces D and E. As shown in FIG. 2, minor surface E has a greater width and perimeter than the minor surface D which results in all five surfaces of the block being of different widths and provides the patient and the body positioning block with a variety of adjustable positions relative to each other and the table as will be more fully described.

Figure 3:
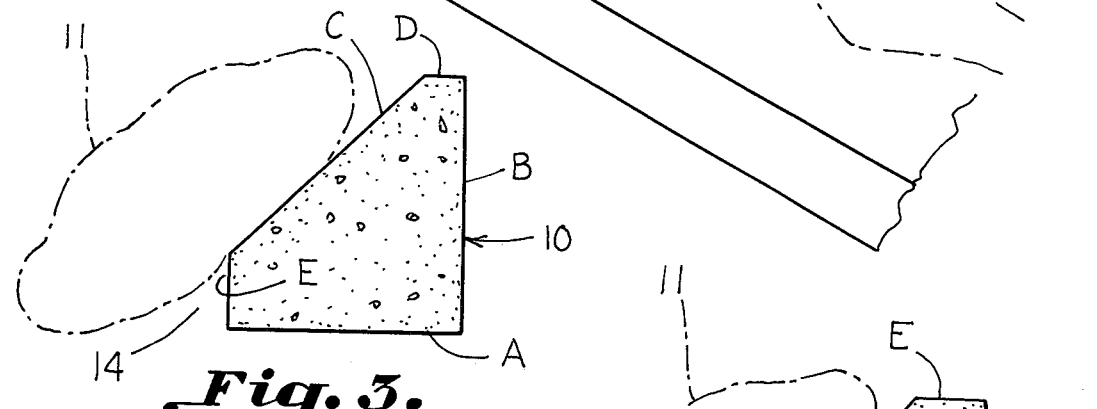
FIG. 3 is an end elevation showing the patient's body with a body position in a third position.
Figure 4:
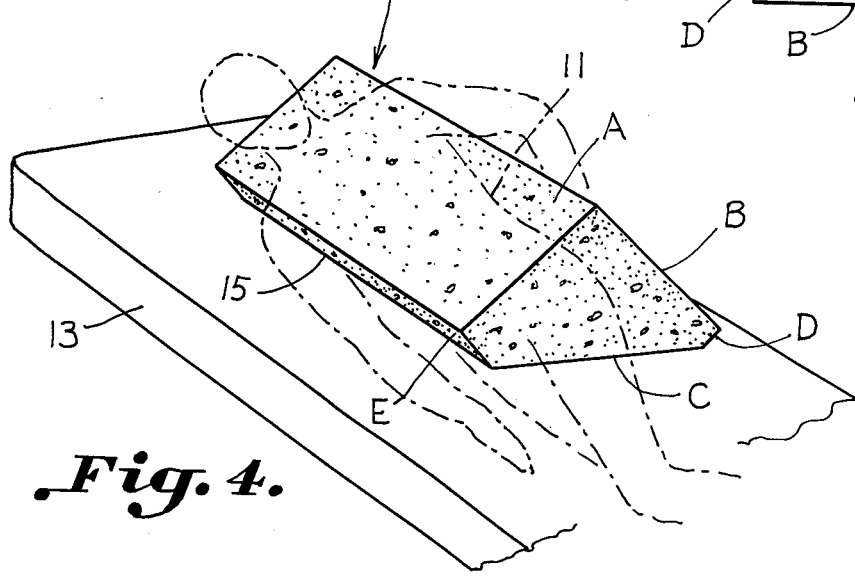
FIG. 4 is a front perspective view showing the patient's body with a body positioner in a fourth position.

In use, the body positioner block can be based on any one of the three major surfaces A, B or C for varying the position of a patient's body on the remaining major surfaces. In FIGS. 1 and 2, the block is based on major surface B providing support for substantially all of the patient's body 11 on major surface C and a rather small void space 12 defined by the patient's body, minor surface D and the table 13. This placement of the block also provides for a wide base surface against the table with a resulting increase in stability. In FIG. 3, the block is based on major surface A providing for less base surface and support surface for the patient on major surface C than shown in the position of FIGS. 1 and 2 but for a greater void space 14 for the increased circulation of air and patient comfort. On base A the block also provides a higher support for a more variable angular positioning of the patient's body 11 against the block 10 and the table 13. In FIG. 4, the block is based on major surface C which provides for positioning and support of the patient's body 11 on either one of the major surfaces A or B. With the patient supported by major surface A, a maximum void space will be provided. In this position, the block can rotate about an edge 15 to provide the greatest variable angular positioning of the patient's body 11 relative to the table. With the patient supported by the major surface B, the maximum surface support will be provided by the block which will also enhance the stability of the patient on the table while providing a lesser void space. Also in this position, the block can be rotatably positioned to provide for additional variety to the side-rotated position of the patient's body.

The length of the body positioner necessarily must be greater that its width for stability and would preferably extend at least from the shoulders to below the waist of the patient. If desired, the reclined patient may be positioned vertically on the side by utilizing a vertical major surface A or B alone or in conjunction with a comparable surface of another support block. With the surface C on the table, either of the surfaces A or B may be utilized to support the patient.

It can thus be seen that the body positioner of the present invention can be used on an operating table or examining table to provide a plurality of support surfaces to adjustably and variably position the body of the patient lying laterally on the table.

While a preferred embodiment of the invention has been described using specific terms, such description is for illustrative purposes only, and it is to be understood that changes and variations may be made without departing from the spirit or scope of the following claims.

What is claimed is:

1. A body positioner for providing lateral support for the body of a patient lying upon an operating table, diagnostic examining table, and the like comprising:
   A. an elongated flexible block structure of resilient deformable polyurethane foam material having an unsymmetrical pentagonal cross-section;
   B. a first major planar surface carried by said block;
   C. a second major planar surface at right angles to said first major surface;
   D. a third major planar surface opposite said first and second major surfaces;
   E. a first minor planar surface joining said third major surface with said first major surface;
   F. a second minor planar surface joining said third major surface with said second major surface;
   G. the said structure having a length greater than its width for supporting a substantial portion of the patient's lateral body length extending from about the shoulders to below the waist for increased stability; and
   H. one of said minor surfaces having a width greater than the width of the other minor surface;
   whereby the structure may be variably based on any one of said major surfaces on the table to provide a variety of lateral body support surfaces for adjustably and stably supporting a patient's body in a variety of lateral body positions to obtain a desired patient body position on the table.

* * * * *